United States Patent [19]

Balisky

[11] Patent Number: 4,989,157

[45] Date of Patent: Jan. 29, 1991

[54] AUTOMATED CHEMICAL MILLING CONTROLLER

[75] Inventor: Todd A. Balisky, Tacoma, Wash.

[73] Assignee: The Boeing Company, Seattle, Wash.

[21] Appl. No.: 693,693

[22] Filed: Jan. 22, 1985

[51] Int. Cl.$^5$ .................. G01N 27/00; G06F 15/46
[52] U.S. Cl. ................... 364/500; 364/579; 422/110; 156/345; 156/627; 204/129.2
[58] Field of Search ............ 364/500, 502, 579; 73/86; 422/108, 110, 111; 204/129.2; 156/345, 627; 324/425

[56] References Cited

U.S. PATENT DOCUMENTS

| | | | |
|---|---|---|---|
| 2,933,675 | 4/1960 | Hoelzle | 324/443 |
| 3,627,661 | 12/1971 | Gordon | 204/300 X |
| 3,826,904 | 7/1974 | Leonard et al. | 364/502 X |
| 3,959,046 | 5/1976 | Bussmann et al. | 156/345 X |
| 4,053,743 | 10/1977 | Niemi | 364/500 |
| 4,055,751 | 10/1977 | Bussmann et al. | 364/500 |
| 4,132,585 | 1/1979 | Oxford | 156/642 X |
| 4,203,156 | 5/1980 | Ishikawa | 364/579 X |
| 4,224,405 | 9/1980 | Hijikata | 364/500 X |
| 4,239,493 | 12/1980 | Niemi et al. | 364/500 X |
| 4,246,171 | 1/1981 | Hamilton et al. | 422/110 X |
| 4,257,439 | 3/1981 | Mageaux | 422/111 X |
| 4,326,940 | 4/1982 | Eckles | 364/579 X |
| 4,338,157 | 7/1982 | Kanda | 156/627 |
| 4,481,061 | 11/1984 | Ross | 156/627 X |
| 4,543,637 | 9/1985 | Smith et al. | 422/111 X |
| 4,616,308 | 10/1986 | Morshedi et al. | 364/500 X |
| 4,654,801 | 3/1987 | Stewart et al. | 364/502 X |

FOREIGN PATENT DOCUMENTS 0628184 9/1978 U.S.S.R. ................ 364/500

Primary Examiner—Joseph L. Dixon
Attorney, Agent, or Firm—John C. Hammar

[57] ABSTRACT

To maintain the actual milling rate of a chemical milling solution within a predetermined range, an automated chemical milling controller periodically measures the actual milling rate within the milling tank, senses the actual temperature of the milling solution, and calculates the normalized milling rate and desired amounts of feedstocks necessary to maintain the milling rate within a predetermined range. The controller automatically adds the desired amounts of feedstocks to a milling solution.

12 Claims, 2 Drawing Sheets

AUTOMATED CHEMICAL MILLING CONTROLLER

TECHNICAL FIELD

The present invention relates to an automated chemical milling controller. An automated method and system for measuring the milling rate of a chemical milling solution uses a suitably programmed microprocessor to measure the actual milling rate of the solution and to feed the desired quantity of feedstocks to the milling solution in response to the actual milling rate.

BACKGROUND ART

Chemical milling or etching accomplishes reduction of the dimensions of a part by the reaction of the chemical milling solution with the immersed part. Control of this milling operation is critical since it is important that the parts be milled to within a close tolerance. Control of the milling operation, however, has proven problematic. For example, in U.S. Pat. No. 2,933,675, Hoelzle discloses a chemical milling controller which measures the conductivity of the milling solution and automatically calculates the respective milling rate and desired immersion time for parts within the milling solution. This control is problematic because it requires a relatively small milling tank, requires recalibration of the instrumentation for use of different solutions and different alloys, and requires recalibration for the milling of parts of different size and shape. Continuous sensing and analysis of the conductivity must be taken since the conductivity of the solution changes continuously as the part is etched. The rate of change of the conductivity is used to calculate the total depth of milling achieved for the part through analog intergration of the rate curve. Since the rate of change is a function of the ratio of the surface area of the part to the volume of the solution, the system is dependent upon the relative sizes of the tank and the respective parts. Parts of different size and shape will produce different rates of change in the conductivity when etched to equal depths, because the parts will have different volumes of metal removed during the milling.

In U.S. Pat. No. 3,959,046, Bussmann et al. disclose another automated chemical milling controller. There, etching solution is withdrawn from the milling tank and is circulated in an etching supply line. Prior to reentry into the milling tank, the etching solution is analyzed to determine the actual milling rate of the recycled solution by having the recycled solution etch through a wire of known composition and known geometric configuration. Based upon the measured milling rate, the time for immersion of parts within the tank is calculated. This control fails to account for differences in performance between the etching solution in the milling tank and the sample lot in the supply line. The method assumes that the solution is well mixed within the tank and that the etching rate is constant as the parts are etched. For these assumptions to be correct, it is necessary that the parts be small and have a relatively short residence time within the tank so that the volume of metal etched from each part is small. Otherwise, the bath composition will change radically during the milling operation, the milling rate will change, and control will be lost. The controller of U.S. Pat. No. 3,959,046 is inadequate for most milling operations, because the assumptions introduce unacceptably large sampling errors.

SUMMARY OF THE INVENTION

An automated chemical milling controller of the present invention measures the normalized milling rate of the solution within the milling tank and automatically adds the desired quantity of feedstocks to the milling solution to maintain the milling rate within a predetermined range in response to the measured milling rate. To measure the normalized milling rate, a consumable sensor is periodically used to measure the actual milling rate of the solution, and the actual milling rate is adjusted to account for the actual temperature of the milling solution. With knowledge of the actual and normalized milling rates (irrespective of the concentration of metal within the milling solution), it is easy to calculate the desired additions of feedstocks to maintain the milling rate within a predetermined range. The rate can be measured periodically on a semi-continuous basis to retain the rate within a working range, thereby allowing precise milling control of a large volume milling tank.

In a preferred embodiment, the tip of a wire of known composition and cross-section is automatically immersed periodically into the actual milling solution within the milling tank. A current is created in the wire upon immersion and this current activates a clock within a dedicated microprocessor. Dissolution of the consumable tip of the wire begins upon immersion and the step in the current above a predetermined threshold triggers the rate measuring cycle. The clock times the dissolution of the wire by sensing the current in the wire, and stops when the current falls below a predetermined minimum which coincides with a milling of the tip reaching a predetermined point. Usually the current falls virtually to zero when the tip of the wire is entirely consumed. The microprocessor calculates the duration of the current cycle and uses this time period to calculate the actual milling rate of the solution.

While the test is occurring, a thermometer senses the actual temperature of the milling solution. The microprocessor uses this temperature data to calculate a normalized milling rate, since the actual milling rate of the solution is a function of its temperature.

From the normalized milling rate, the microprocessor calculates the desired amount of feedstocks which are necessary to add to the milling solution to maintain the actual milling rate within a predetermined range. With the amounts calculated, the microprocessor activates an automatic feed system (consisting of a reservoir for each feedstock, a pump associated with each reservoir, and a flow sensor in the feed line from the reservoir to the milling solution to allow feedback control of the pump). The desired amount of feedstocks are automatically added to milling solution to maintain its milling rate, irrespective of the build up of metal within the milling solution.

For a milling operation using about 1000 gallons of milling solution, tests are run approximately every 4 hours and the necessary adjustments are made, usually by adding about 10 gallons of feedstocks (1% of the bath) to the solution. If desired, the period between tests can be reduced to as short as 20 minutes to achieve more accurate control of the actual milling rate.

The invention provides a convenient control for large milling operations by automatically maintaining the milling solution within a desired range. With this control, accurate milling can be achieved at substantial savings.

BEST MODE CONTEMPLATED FOR CARRYING OUT THE INVENTION

Figure 1:
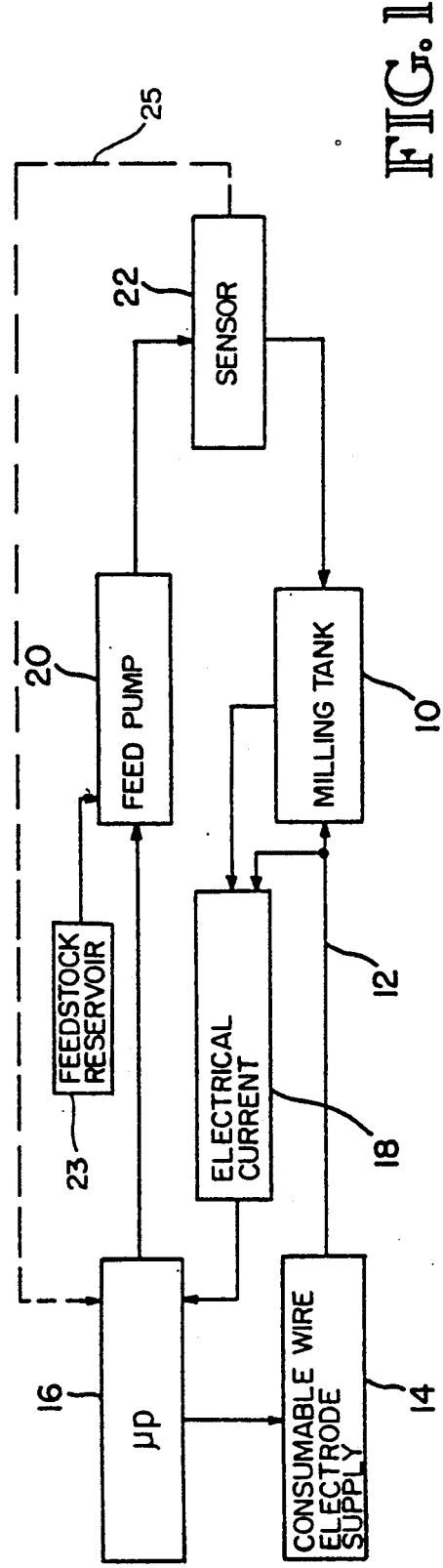
FIG. 1 is a schematic of a preferred automated chemical milling controller of the present invention.

An automated chemical milling controller operates through the schematic process illustrated in FIG. 1. In a milling tank 10 which contains the applicable milling solution and parts to be milled, the actual milling rate of the solution is sensed with a consumable wire electrode 12 fed periodically from a supply 14 as signaled by the microprocessor 16. Upon immersion into the milling solution, an electrical current 18 is detected in the wire electrode 12 since current is supplied to the milling solution with another electrode 26 (FIG. 2 from a current supply 29. The step in current 18 activates a clock within the microprocessor 16, which measures the consumption time until the current steps downwardly, usually to zero, when the clock is deactivated. The time data is directly proportional to the actual milling rate of the solution. The microprocessor 16 converts the time data into milling rate data necessary for calculating the normalized milling rate.

Simultaneously with sensing of the actual milling rate of the solution, the actual temperature of the milling solution is determined, and this temperature data is also transferred to the microprocessor 16. Since the activity of the solution is a function of the temperature, the normalized milling rate can be calculated from the actual milling rate and the temperature of the solution and the desired quantity of feedstocks that should be fed to the milling tank 10 to maintain the actual or normalized milling rate within a predetermined range can also be calculated directly. The microprocessor 16 signals a feed pump 20 to draw the desired quantity of feed from a feedstock reservoir 23 and to direct the feedstock to the milling tank 10. A flow sensor 22 between the feed pump 20 or reservoir 23 and the milling tank 10 senses the quantity of feedstock actually pumped and provides the microprocessor 16 with this feedback control data 25. In this way, accurate addition of the proper quantity of feedstock is easily achieved.

Figure 2:
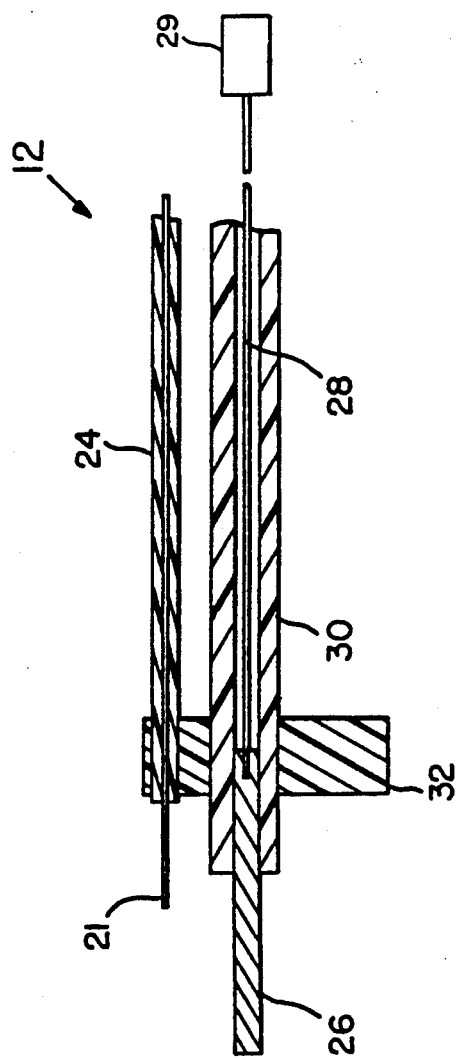
FIG. 2 is a sectional schematic of a preferred consumable sensor of the present invention.

As shown in FIG. 2, the milling rate sensor electrode 12 comprises a wire 21 of known composition and configuration, usually having a circular cross section so that the rate of milling is directly proportional to the diameter of the wire. Also, the wire is generally of the same composition as the parts to be milled, although with suitable empirical data, it is possible to correlate the milling rate for any known composition wire with any part composition in the solution. It is highly preferred to match the composition of the wire with that of the milled parts.

The wire 21 extends from the end of a plastic guide tube 24 adjacent to a carbon electrode 26 which is connected to an Inconel wire 28 within a TEFLON (a duPont Trademark) insulator 30. Both the carbon electrode 26 and sensor wire 21 are mounted within a plastic block 32 for immersion within the milling solution. The block 32 may be positioned a fixed distance above the liquid level within the milling tank or the block may be mounted on a float which will automatically control the height of the block above the liquid within the milling solution.

The sensor wire 21 is freely moveable within the plastic guide tube 24 so that a new portion of wire may be automatically extended from the supply 14 upon signal from the microprocessor 16. Because the wire 21 is circular in cross-section, the milling rate may be determined without reference to the length of the wire immersed within the solution. All that is required is an accurate measure of the time required to eat through the circular cross-section. As will be understood, other geometric configurations might be used as desired with empirical data regarding their etch rates, but it is convenient to use a conventional wire.

Figure 3:
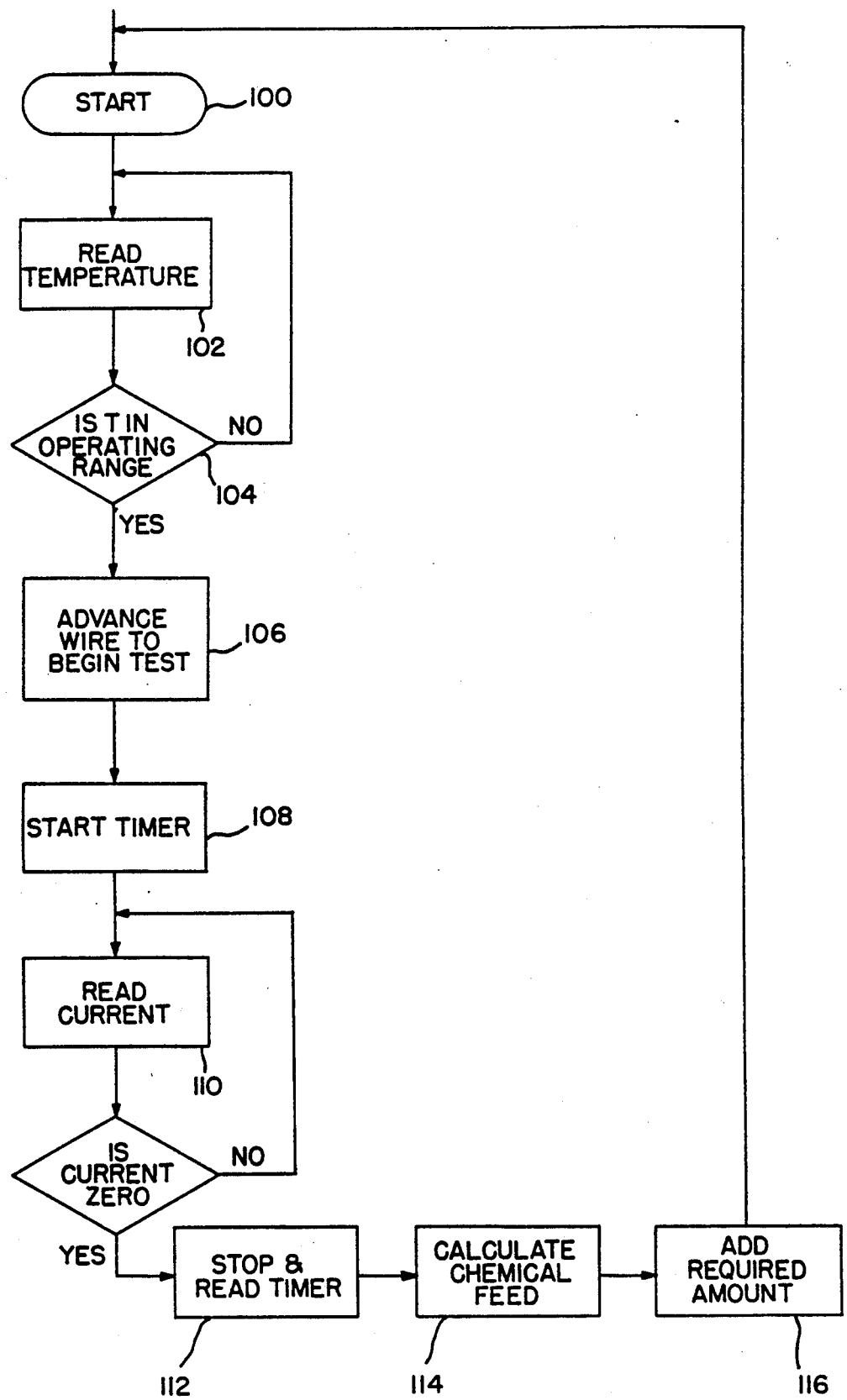
FIG. 3 is a software block diagram for the controller of FIG. 1.

As illustrated in FIG. 3, the microprocessor 16 begins the control sequence (block 100) by reading the temperature of the milling solution (block 102) and determining whether the measured temperature is within the desired operating range (block 104). If within the operating range, the microprocessor 16 will advance a small segment of the the sensor wire 21 into the milling solution from the supply 14 through a motor drive (block 106). If outside the range, the solution will be heated or cooled, as required. Upon immersion of the tip of the wire sensor 21 into the solution, a current 18 will be generated in the wire 21 and this current 18 will trigger a timer within the microprocessor 16 (block 108). The current detector within the microprocessor 16 will continue to read the current during dissolution of the tip of the wire 21. When the current drops below a predetermined level, such as when an open circuit results from dissolution of the wire tip, the current detector will automatically stop the timer as indicated by blocks 110, 111 and 112.

Upon stopping of the clock, the microprocessor 16 will automatically calculate the actual milling rate of the solution, the normalized milling rate, and the quantity of feedstocks which must be added to the solution to maintain the milling rate within a predetermined range (block 114). The microprocessor will then activiate the pump 20 (FIG. 1), which will deliver the desired quantity of feedstock from the reservoir into the milling solution (block 116), completing one control cycle.

Generally, the milling solution tank 10 will contain about 1000 gallons of milling solution and the milling rate will be monitored every four hours. Because of the large volume of milling solution, the rate of change of the mill rate is slow. Periodic measurements of relatively long frequency, such as four hours, are generally adequate to monitor the milling solution rate and to maintain it within a narrow range suitable for precise calculation of milling. For smaller tanks or strongly active milling solutions, however, the monitoring period must be much shorter since the rate of change of the milling rate is greater. With monitoring on a four hour period, it is common that about 10 gallons (1% of volume) of feedstock will be added to the 1,000 gallon milling solution each cycle. Such additions show that the control is precise and that the milling rate of the solution remains within a narrow range.

The control equations are:

(I) Actual Milling Rate $$M = R/dt$$

wherein $M$ = actual milling rate;

R = wire radius; and
dt = elapsed dissolution time (II) Normalized Milling Rate $$M_n = M + (dM)(T_o - T),$$

wherein
M = actual milling rate, eqn. I;
$M_n$ = normalized milling rate;
$T_o$ = reference temperature, °F.;
T = measured temperature, °F.; and
dM = rate of change of milling rate/deg. F.

(III) Feedstock Quantity $$F = (M_o - M_n)(F_o)(V)$$

wherein
F = Feed quantity;
$M_o$ = milling rate at feed rate $F_o$ and $T_o$;
$M_n$ = normalized milling rate, eqn. II;
$F_o$ = feed rate at $T_o$;
V = volume of milling solution.

$F_o$ is the quantity of feed necessary to achieve the milling rate ($M_o$) at the setpoint temperature of the solution ($T_o$) per unit volume of the milling solution.

The invention is best illustrated, perhaps, by the following example drawn from pilot plant operation of the controller.

EXAMPLE 1

A milling solution for treating 6% Al, 4% V titanium alloy or other metals or alloys was made up by mixing 4.0 gallons of technical grade hydrofluoric acid, 0.5 gallons of technical grade nitric acid, and 2 lbs. of titanium metal. A wetting agent was added and the solution was brought to 100 gallons by adding the necessary water.

The milling rate sensor used a 6% Al, 4% V titanium alloy wire having a diameter of 0.035 in. The actual milling rate was measured about every four hours during operation of the milling tank and the necessary quantities of hydrofluoric and nitric acids were added to maintain the etch rate between about 0.90–0.95 mil/-side/min. Hydrofluoric acid is used to increase the etch rate. Nitric acid is used to suppress the etch rate.

Calculations for the automatic additions of HF were based upon the following empirical constants:
$T_o$ = 115° F.
dM = 0.0000024 in/min-deg F.
$M_o$ = 0.0015 in/min
$F_o$ = 50 gal HF/(in/min) - gal bath Periodically a portion of the milling solution was purged. Control was easily achieved to hold the bath within the desired etch rate range.

Those skilled in the art will readily recognize modifications which might be made to the general concept of the present invention. Therefore, the invention should be construed broadly in light of the accompanying description and drawings. The description of preferred embodiments illustrates the invention and should not limit it, unless such limitation is necessary in view of the pertinent prior art.

I claim:

1. An automated method for measuring and controlling the milling rate of a chemical milling solution using a suitably programmed microprocessor as a controller, comprising the steps of:

(a) measuring the time needed to etch a known portion of a known alloy test specimen that is immersed in the solution;
   (b) calculating in the microprocessor the actual milling rate of the solution based on the measured time;
   (c) calculating in the microprocessor the normalized milling rate by adjusting the actual milling rate of step (b) in response to the actual temperature of the solution in the tank according to the formula:

$$M_n = M + (dM)(T_o - T)$$

wherein
   M = actual milling rate;
   $M_n$ = normalized milling rate;
   $T_o$ = reference temperature;
   T = measured temperature; and
   dM = rate of change of milling rate/deg.

(d) from the normalized milling rate, automatically calculating in the microprocessor the desired quantity of feedstocks needed to maintain the milling rate of the solution within a predetermined range; and
   (e) signaling a feed pump from the microprocessor to activate the pump and to add the necessary quantity of that feedstock to the solution.

2. The automated method of claim 1 wherein the step of measuring the time includes the substeps of:
   (a) immersing the portion of the test specimen into the solution;
   (b) activating a clock by and upon immersing the specimen into the solution; and
   (c) deactivating the clock upon dissolution of the immersed portion of the sensor; and
   (d) determining the elapsed time during which the clock was activated.

3. The automated method of claim 2 further comprising the step of immersing a reference electrode in the solution adjacent the portion of the test specimen, wherein the clock is activated by detecting a current in the immersed portion, and wherein the clock is deactivated by the current falling below a predetermined threshold.

4. The automated method of claim 1 wherein steps (a) through (e) are automatically repeated periodically by the microprocessor to monitor the milling rate of the solution in a semi-continuous basis during a continuous milling operation.

5. The automated method of claim 1 wherein the specimen is an Al/V titanium alloy and the feedstock is selected from hydrofluoric acid or nitric acid.

6. An automated method for measuring and controlling the milling rate of a chemical milling solution within a predetermined range using a suitably programmed microprocessor, comprising the steps of:
   (a) measuring the actual milling rate of the solution within the milling tank by dissolving a known portion of a sensor in the tank;
   (b) calculating in the microprocessor the normalized milling rate for the solution by adjusting he actual milling rate in response to the measured temperature of the solution; and
   (c) automatically adding a predetermined amount of at least one feedstock to the solution to maintain the milling rate within a predetermined range in response to the normalized milling rate, the microprocessor signalling a pump associated with the feedstock to activate the pump to supply feedstock to the tank.

7. The automated method of claim 6 wherein the step of measuring includes the substeps of:
   (a) immersing the portion of the sensor in the solution int he tank adjacent to a reference electrode, the portion having predetermined physical characteristics allowing calculation of the milling rate from the rate of dissolution of a predetermined portion of the sensor;
   (b) detecting a current in the sensor upon immersing the portion, the current flowing from the electrode through the solution to the sensor;
   (c) activating a clock upon sensing the current; and
   (d) deactivating the clock when the current falls below a predetermined threshold, the drop in current corresponding to dissolution to the predetermined portion of the sensor.

8. The method of claim 7 wherein the step of adding feedstock includes the substeps of:
   (a) calculating in the microprocessor the desired quantity of feedstock based upon the normalized milling rate;
   (b) automatically withdrawing the quantity of step (a) from a reservoir with the pump; and
   (c) adding that quantity to the solution.

9. An automated method for measuring and controlling the milling rate of a chemical milling solution within a predetermined range, thereby allowing accurate control of the milling achieved during the milling operation, comprising the steps of:
   (a) immersing, adjacent a reference electrode, the tip of an alloy wire into the solution within the milling tank, the wire having a known cross-section, the immersion occurring by advance of the wire under the control of a microprocessor;
   (b) detecting a current in the wire above a predetermined threshold and activating a clock in the microprocessor in response to the detected current;
   (c) measuring the elapsed time to dissolve the tip of the wire by continuously sensing the current and running the clock until the current falls to an open circuit current;
   (d) automatically calculating in the microprocessor the actual milling rate using the elapsed time;
   (e) measuring the actual temperature of the solution within the milling tank;
   (f) normalizing the calculated milling rate of step (d) in response to the measured temperature;
   (g) automatically calculating in the microprocessor the desired amount of at least one feedstock to add to the solution to maintain the milling rate within a predetermined range, the calculation being based on the normalized milling rate of step (f); and
   (h) automatically adding the desired amount of feedstock to the solution by having the microprocessor activate a pump connected to a reservoir of the feedstock.

10. The automated method of claim 9 wherein steps (a) through (h) are repeated periodically by the microprocessor during the milling operation to monitor the milling rate on a semi-continuous basis.

11. An automated system for monitoring and controlling the milling rate of a chemical milling solution during a milling operation, comprising:
    (a) a supply of wire of known composition and cross-section;
    (b) means for immersing a predetermined portion of the wire into the solution on the milling tank at predetermined, periodic intervals;
    (c) means for creating a current within the wire upon immersion of the wire into the solution in the milling tank;
    (d) a clock activated by a current in the wire above a predetermined threshold;
    (e) means for deactivating the clock when the current falls below a second threshold, the threshold indicating milling of a predetermined portion of the wire;
    (f) means for calculating the actual milling rate of the solution automatically in response to the elapsed time measured with the clock;
    (g) means for normalizing the milling rate in response to the actual temperature of the solution in the milling tank; and
    (h) means for adding a predetermined quantity of a feedstock from a reservoir into the solution in response to the normalized milling rate of step (g), the quantity maintaining the milling rate within a predetermined range.

12. The system of claim 11 further comprising a feedback controller for measuring the feedstock withdrawn from the reservoir and added to the solution.

* * * * *